United States Patent [19]

Lin et al.

[11] Patent Number: 4,794,199

[45] Date of Patent: Dec. 27, 1988

[54] PROCESS FOR SYNTHESIS OF PRIMARY AMINES FROM OLEFINS, SYNGAS AND AMMONIA

[75] Inventors: Jiang-Jen Lin, Round Rock; John F. Knifton, Austin, both of Tex.

[73] Assignee: Texaco Inc., White Plains, N.Y.

[21] Appl. No.: 105,462

[22] Filed: Oct. 1, 1987

Related U.S. Application Data

[63] Continuation of Ser. No. 628,104, Jul. 5, 1984, abandoned.

[51] Int. Cl.⁴ .................... C07C 85/08; C07C 85/18
[52] U.S. Cl. .................................. 564/467; 564/485
[58] Field of Search ............................. 564/467, 485

[56] References Cited

U.S. PATENT DOCUMENTS

| | | | |
|---|---|---|---|
| 2,497,310 | 2/1950 | Larson | 564/467 |
| 4,322,530 | 3/1982 | Jachimowicz | 564/467 |
| 4,334,042 | 6/1982 | Matsumoto et al. | 564/467 |

FOREIGN PATENT DOCUMENTS 0092839  7/1981  Japan ................................ 564/467

Primary Examiner—Glennon H. Hollrah
Assistant Examiner—John A. Sopp
Attorney, Agent, or Firm—Jack H. Park; Kenneth R. Priem; Cynthia L. Kendrick

[57] ABSTRACT

This invention concerns the synthesis of primary amines from olefins, synthesis gas and ammonia via an amination process in the presence of a cobalt catalyst, an ether solvent and a tertiary group VB donor ligand.

2 Claims, No Drawings

PROCESS FOR SYNTHESIS OF PRIMARY AMINES FROM OLEFINS, SYNGAS AND AMMONIA

FIELD OF THE INVENTION

This invention concerns a process for converting ammonia, syngas and olefins to primary amines.

More particularly, this invention relates to the catalytic amination of olefins such as, for example, terminally unsaturated, α-olefins to primary amines by a process comprising adding hydrogen and carbon monoxide to said olefinic substrates in the presence of a catalyst comprising a cobalt-containing compound, a solvent and a phosphorus-containing ligand.

BACKGROUND OF THE INVENTION

The present invention is directed to a process of forming primary amines from olefins, synthesis gas and ammonia.

In the past lower aliphatic amines have generally been prepared by one of four commercial processes. In one process, alcohols are reacted with ammonia in the presence of a dehydrating agent, such as alumina to produce a primary, secondary or tertiary amine depending on the ratio of reactants used. A second commercial method comprised reacting an alcohol with ammonia in the presence of hydrogen and a hydrogenation catalyst, such as nickel. This method normally produced a mixture of amines.

A third method required the reaction of aldehydes with ammonia and hydrogen in the presence of a hydrogenation catalyst such as copper or nickel. Again, the product was a mixture of amines. The commercial method of forming fatty amines was accomplished by reacting a fatty acid or its ester with ammonia to form the nitrile and then hydrogenating the nitrile to form the amine.

The principle of obtaining amines starting from an olefin, hydrogen, CO and ammonia or substituted ammonia is known. See U.S. Pat. Nos. 2,422,631, 2,497,310 and 3,513,200. In these processes the selectivity for amines is only moderate and the selectivity to primary amines is poor.

U.S. Pat. No. 4,096,150 discloses a process for preparation of tertiary amines in high selectivity by reacting an olefin, hydrogen and CO with a secondary amine in the presence of a coordination complex catalyst of a Group VIII metal and a ligand, the donor atom of which is oxygen, nitrogen or sulfur.

Processes for producing secondary and tertiary amines are also taught in the following: U.S. Pat. No. 4,250,115 which uses a rhodium or ruthenium-containing catalyst; *J. Org. Chem.* 1980, 45, 3370-3372 which discusses the use of a variety of Group VIII transition-metal carbonyl catalyst precursors, including the novel mixed-metal ruthenium/iron; and *J. Org. Chem.* 1982, 47, 445-447 which discloses a high yield one step process for synthesis of tertiary and secondary amines from olefins, carbon monoxide, water and a nitrogen source using a rhodium-based compound as a catalyst.

U.K. patent application No. GB 2.070010 A discloses a process for producing secondary amines by reacting an olefinic compound, carbon monoxide, ammonia and water in an inert liquid medium in the presence of a catalyst comprising Rh or a Rh salt, carbonyl, oxide or complex.

Aminomethylation of olefins using carbon monoxide and water is disclosed in U.S. Pat. No. 4,292,242 wherein a mixed ruthenium carbonyl, iron carbonyl catalyst is employed.

There seems to be little art on the production of primary amines from synthesis gas, water and ammonia. Large quantities of linear alkyl primary amines are presently produced from the natural fatty acids in coconut oil, palm oil, tallow, etc. The market for these amines exceeds 100 mm lbs/yr. with applications in the rubber and detergent industries as chemical intermediates.

In U.S. Pat. No. 4,299,985, a process is disclosed which is a two-step process for producing linear alkyl primary amines from alpha olefins via oxoamination process comprising the addition of hydrogen and carbon monoxide to olefins in the presence of ligand-stabilized platinum(II) halide catalysts with Group IVB metal halide cocatalysts and reductive amination of said aldehydic intermediates in the presence of oxide supported nickel catalysts.

Japan Kakai Tokkyo Koho No. 81 92,839 to Mitsubishi discloses a process where primary amines were prepared by treating α-olefins ($C_n$) with CO, $H_2$ and $NH_3$ in an alcohol solvent containing cobalt and a tertiary phosphine. In this procedure the selectivity for $C_{n+1}$ primary amines was moderate, about 30%. The production of $C_{2n+2}$ primary amines is not reported in this patent.

It would be a considerable advance in the art to produce much desired primary amines from easily obtainable and inexpensive reactants such as synthesis gas and ammonia using catalysts which would be commercially economical. In addition, it would be a considerable advance in the art to obtain selectivities for primary amines which are much improved over other methods used in the art.

SUMMARY

It has now been discovered that synthesis of primary amines can be carried out without the above-mentioned drawbacks by using the process according to the present invention. This invention provides for preparation of primary amines from an olefin, syngas and ammonia by using an improved process which leads to better selectivity.

It has been discovered that improved results are obtained by the use of particular solvents and ligands in conjunction with a catalyst system comprising a cobalt-containing compound. The system comprises reacting an olefin, syngas and ammonia in the presence of a cobalt catalyst, an ether solvent and a group VB donor ligand at a pressure of at least 100 psig and a temperature of greater than 50° C.

In this process 1 hexene is the preferred olefin and selectivity to $C_7$ and $C_{14}$ amines is on the order of 57% totaled.

The accomplishment of the above-mentioned ends as well as other new and useful objectives is described in greater detail below, by way of the following exemplary and non-limitative descriptions of various embodiments.

DETAILED DESCRIPTION

In the narrower and more preferred practice of this invention, primary amines are prepared from an olefin, synthesis gas (mixture of carbon mnnoxide and hydrogen) plus ammonia by a process comprising:

(a) Contacting said mixture of olefin, carbon monoxide, hydrogen and ammonia with a catalyst system comprising an ether solvent containing a cobalt-containing compound and a phosphine ligand, (b) heating said reaction mixture to a temperature of at least 150° C. and a pressure of at least 500 psig and (c) separating said primary amines contained therein.

In order to present the inventive concept in the greatest possible detail to promote its understanding, the following supplementary disclosure is submitted. The basic invention improved upon here is practiced as follows:

Catalysts which are suitable in the practice of this invention contain cobalt. The cobalt-containing catalyst may be chosen from a wide variety of organic or inorganic compounds, complexes, etc. It is only necessary that the catalyst precursor actually employed contain said metal in any of its ionic states. The actual catalytically active species is then believed to comprise cobalt in complex combination with carbon monoxide, hydrogen, phosphine ligand and solubilized in an inert solvent. The most effective catalyst is believed to be achieved where cobalt carbonyls are mixed with phosphine ligands under reaction conditions.

The cobalt catalyst precursors may take many different forms. For instance, the cobalt may be added to the reaction mixture in the form of an oxide, salt, carbonyl derivative and the like. Examples of these include, among others, cobalt oxides $Co_2O_3$, $Co_3O_4$, $CoO$, cobalt(II) bromide, cobalt(II) thiocyanate, cobalt(II) hydroxide, cobalt(II) carbonate, cobalt(II) nitrate, cobalt(II) phosphate, cobalt acetate, cobalt napthenate, cobalt benzoate, cobalt valerate, cobalt cyclohexanoate, cobalt carbonyls, such as dicobalt octacarbonyl $Co_2(CO)_8$, tetracobalt dodecacarbonyl $Co_4(CO)_{12}$ and hexacobalt hexadecacarbonyl $Co_6(CO)_6$ and derivatives thereof by reaction with ligands and preferably group V donor ligands such as $(Co(CO)_3L)_2$ wherein L is $PR_3$, $AsR_3$ and $SbR_3$, wherein R represents a hydrocarbon radical, cobalt carbonyl hydrides, cobalt carbonyl bromide, cobalt nitrosyl carbonyls such as $CoNO(CO)_3$, $Co(NO)(CO)_2PPh_3$, cobalt nitrosyl bromide, organometallic compounds obtained by reacting cobalt carbonyls with olefins and allyl and acetylene compounds.

Preferred cobalt-containing compounds to be used in the catalyst system comprise those having at least one cobalt atom attached to carbon, such as the cobalt carbonyls and their derivatives such as, for example, dicobalt octacarbonyl, tetracobalt dodecacarbonyl, $(Co(CO)_3P(CH_3)_3)_2$, organometallic compounds obtained by reacting the cobalt carbonyls with olefins, cycloolefins, allyl and acetylene compounds such as cyclopentadienyl cobalt dicarbonyl, cobalt carbonyl bromides, cobalt carbonyl hydrides, cobalt nitrosyl carbonyls and the like and mixtures thereof.

Particularly preferred cobalt-containing compounds to be used in the catalyst comprise cobalt carbonyls such as dicobalt octacarbonyl and tetracobalt dodecacarbonyl.

The cobalt-containing compound is preferably complexed with a suitable ligand containing one or more group VB donor atoms per molecule. Preferably said ligands should contain one or more tertiary phosphorus atoms per molecule. Examples of effective phosphine-containing ligands include tri-n-butylphosphine, triethylphosphine, tri-n-octylphosphine, bis(1,2-diphenylphosphino)ethane, triphenylphosphine, tri-p-tolylphosphine, bis(1,3-diphenylphosphino)propane, methyldiphenylphosphine, tribenzylphosphine, tri-t-butylphosphine and vinyldiphenylphosphine.

The preferred phosphine ligand is tri-n-butylphosphine.

Said phosphine-containing ligands may optionally be employed in the presence of an aliphatic amide, such as acetamide, formamide and N,N-dimethylformamide.

The olefinic substrates employed in the practice of this invention include unsaturated hydrocarbons containing from 2 up to 30 carbon atoms per molecule and having at least one olefinic group therein. It is preferred that the olefinic compound contains a single olefinic group and further that the olefinic group is terminally positioned (that is it is an α-olefin). The olefinic substrate may also contain alicyclic, arylic, alkarylic and acyclic hydrocarbyl groups within the hydrocarbon moiety. Examples of suitable α-olefin substrates are compounds such as propylene, butene-1, pentene-1, hexene-1, heptene-1, octene-1, decene-1, dodecene-1, tridecene-1, tetradecene-1 and higher 1-olefins up to 30 carbon atoms. Best results are obtained using the 1-olefins with two to fourteen carbon atoms. Particularly preferred is 1-hexene.

The nitrogen source is required to be ammonia which can be either in liquid or gaseous form and can be either anhydrous or as an aqueous solution. It has been found that the use of ammonia, in combination with other required agents produces primary amines in good yields.

The reaction is performed under liquid phase conditions. The suitable organic liquid solvent can be employed which is inert to the reaction conditions, the catalyst and the product. Examples of suitable solvents that can be used in accordance with this invention are those solvents containing one or more ether linkages per molecule. Ethers which may be utilized as solvents include cyclic, acyclic and heterocyclic materials. Preferred ethers are the heterocyclic ethers as illustrated by 1,4-dioxane (p-dioxane) and 1,3-dioxane. Other suitable ether solvents include N-butyl vinyl ether, vinyl phenyl ether, ethyl vinyl ether, isopropyl propyl ether, diethylene glycol dibutyl ether, dibutyl ether, ethyl butyl ether, diphenyl ether, heptyl phenyl ether, anisole, tetrahydrofuran, tetraglyme, etc. The most useful solvents of all of the above groups include the ethers as represented by monocyclic, heterocyclic ethers, including 1,4-dioxane or p-dioxane, etc. and tetraglyme.

The quantity of cobalt catalyst employed in the instant invention is not critical and may vary over a wide range. In general, the novel process is desirably conducted in the presence of a catalytically effective quantity of the active cobalt species and phosphine ligand which gives the desired products in reasonable yields. The reaction proceeds when employing as little as about $1 \times 10^{-6}$ weight percent, and even lesser amounts, of cobalt together with at least $1 \times 10^{-6}$ weight percent of phosphine ligand, basis the total weight of the reaction mixture. The upper concentration is dictated by a variety of factors including catalyst cost, partial pressures of carbon monoxide and hydrogen, operating temperature etc. A cobalt catalyst concentration of from about $1 \times 10^{-5}$ to about 10 weight percent cobalt in conjunction with an phosphine ligand concentration of from about $1 \times 10^{-5}$ to about 10 weight percent, based on the total weight of reaction mixture is generally desirable in the practice of this invention. The preferred cobalt to phosphine ligand atomic ratio is about 1:0.1 to 1:10.

The temperature range which can usefully be employed in these syntheses is a variable dependent upon other experimental factors, including the pressure, the concentration and the choice of the particular species of cobalt catalyst among other things. The range of operability is from about 50° to 300° C. when superatmospheric pressures of syngas are employed. A narrow range of 150°-250° C. represents the preferred temperature range. Superatmospheric pressures of 100 psi or greater lead to substantial yields of primary amines by the process of this invention. A preferred operating range is above 500 psi. The most preferred range is from 500-2000 psi, but pressures greater than 2000 psi can be used.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases of the group including nitrogen, argon, neon and the like, or they may include gases that may or may not undergo reaction under CO hydrogenation conditions, as represented by carbon dioxide and hydrocarbons including methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired oxonation reaction.

The novel process of this invention can be conducted in a batch, semi-continuous or continuous fashion and said material may be recovered by methods well known in the art, such as distillation, fractionation, extraction and the like.

The major products of these syntheses are primary amines, particularly primary aliphatic amines, having a carbon number either one greater ($C_{n+1}$) than the starting olefin substrate ($C_n$) and/or a carbon number two greater than twice the carbon number ($C_{2n+2}$) of the starting olefin. The principal by-products of these preparations are the corresponding alcohols. For example, where 1-hexene is the starting olefin, the principal primary amine products are the corresponding linear and branched heptylamines and tetradecylamines, while the by-products are the C-7 and C-14 alcohols. Some hydrocarbon may also be detected in certain cases.

The synthesis of both $C_{n+1}$ and $C_{2n+2}$ aliphatic amines in the present invention using the cobalt-phosphine catalyst combinations solubilized in ether solvents is in contrast to the prior art where carboamination of α-olefins is reported to yield only $C_{n+1}$ primary aliphatic amines (see for example, Japan Kakai Tokkyo Koho 81 92,839).

The products have been identified in this work by one or more of the following analytical procedures, viz, gas-liquid phase chromatography (glc), infrared (ir), mass spectrometry, proton nuclear magnetic resonance (H'-nmr) and elemental analyses, or a combination of these techniques. All temperatures are in degrees centigrade and all pressures are in pounds per square inch gauge (psig).

Having described the inventive process, the following examples are submitted to supply specific and illustrative embodiments.

EXAMPLE 1

A glass-lined pressure reactor (183 ml) was charged with a mixture of dicobalt octacarbonyl (0.34 g, 1.0 mmole), triphenylphosphine (0.80 g, 4.0 mmole), 1-hexene (7.0 g) and p-dioxane (7.0 g). The reactor was purged of air and then charged with anhydrous ammonia (~10 g) and syngas (CO/$H_2$=1:2 molar ratio) to 500 psi. The reactor was heated to 200° C. while it was agitated by rocking. The pressure was brought up to 2000 psi by the addition of CO/H2 mixtures. The reaction was held at temperature for 4.0 hours; during this period the pressure dropped to 1500 psi. The reactor was allowed to cool to room temperature. The excess gas was vented from the reactor, following which 13.0 of yellow solution with a ca. 0.3 g bottom layer was recovered. A metal deposit on the wall of glass liner was observed.

The product liquid was analyzed by glc. The conversion of 1-hexene was calculated to be ~85%. The principal products and their selectivities were assigned as follows:

| | | |
|---|---|---|
| $C_7$-Primary Amines | $CH_3CH_2CH_2CH_2CH_2CH_2CH_2NH_2$ $CH_3CH_2CH_2CH_2CHCH_2NH_2$ $\quad\quad\quad\quad\quad\quad\quad\; |$ $\quad\quad\quad\quad\quad\quad\quad CH_3$ | 32% |
| | C-7 primary alcohols | 15% |
| | $CH_3CH_2CH_2CH_2CH_2\!-\!CHCH_3$ $\quad\quad\quad\quad\quad\quad\quad\quad\quad\;\, |$ $CH_3CH_2CH_2CH_2CH_2CH_2CH_2$ | 11% |
| $C_{14}$-Primary Amine | $CH_3\!-\!CH_2\!-\!CH_2\!-\!CH_2CH_2CH\!-\!CH_2NH_2$ $\quad\quad\quad\quad\quad\quad\quad\quad\quad\quad\quad\;\; |$ $CH_3CH_2CH_2CH_2CH_2CH_2CH_2$ | 25% |
| | C-14 primary alcohols | 7% |

It may be noted that in this example using the dicobalt octacarbonyl-triphenylphosphine catalyst in p-dioxane solvent the principal products from the reaction of 1-hexene, syngas and ammonia are the corresponding heptyl primary amines plus tetradecyl primary amines. The heptylamine product fraction may comprise both primary and secondary alkyl primary amines.

The total selectivity to primary amines in this Example is estimated to be 57%.

EXAMPLE 2

A reactor was charged with a mixture of dicobalt octacarbonyl (0.68 g, 2.0 mmoles), tri-n-butylphosphine (1.6 g, 8.0 mmoles), 1-hexene (14.0 g) and p-dioxane (14.0 g). The procedures of Example 1 were repeated except using 40.0 g of ammonia. Under the reaction conditions of CO/$H_2$=1:2 molar ratio, 2000 psi, 200° C. and 4 hours, the product solution contained C-7 primary amine at 28% selectivity C-7 alcohol at 4% selectivity, C-14 primary amine at 1% selectivity and C-14 alcohol at 1% selectivity. The 1-hexene conversion was ca. 30%.

It is noted that the use of a large excess of ammonia produced C-7 amine as the major product and C-14 product at only relatively low yield.

EXAMPLE 3

The experimental procedures in Example 1 were repeated except using $Co_2(CO)_8$ (0.68g, 2.0 mmoles), n-$Bu_3P$ (0.40 g, 2.0 mmoles), 1-hexene (14.0 g), p-dioxane (14.0 g) and ammonia (13.0 g). The reaction conditions of 1650 psi, $CO/H_2 = 1:2$ 200° C. and 4 hours were employed. The recovered product solution (30.5 g) was analyzed. The product selectivities were calculated to be 6% for C-7 primary amine, 11% for C-7 alcohol, 4% for C-14-primary amine and 8% for C-14 alcohol. The olefin conversion was 73%.

By using a relatively small amount of ammonia, the high olefin conversion was observed although the primary amine selectivity was lower.

EXAMPLE 4

The same experimental procedures were employed except using $Co_2(CO)_8$ (0.68 g, 2.0 mmoles), n-$Bu_3P$ (1.6 g, 8.0 mmoles) 1-hexene (14.0 g), p-dioxane (14.0 g), acetamide (1.0 g) and ammonia (12.5 g). The reaction conditions were 2000 psi-1800 psi, $CO/_2 = 1:2$, 200° C. and 4 hours. The recovered product solutions (34.5 g) contained the following products: C-7 primary amine (7% selectivity), C-7 alcohol (15% selectivity), C-14 primary amine (7% selectivity, and C-14 alcohol (13% selectivity). The olefin conversion was 81%.

The presence of acetamide has the tendency to stabilize the cobalt catalyst so that the conversion of olefin is higher.

EXAMPLE 5

The experimental procedures were repeated except using tetraglyme as the solvent. The charged mixture was $Co_2(CO)_8$ (0.68 g, 2 mmoles), n-$Bu_3P$ (1.6 g 8.0 mmoles), 1-hexene (14.0 g), terraglyme (14.0 g) and ammonia (20 g). The reaction conditions were 200° C., 2000 psi, $CO/H_2 = 1:2$ and 4 hours. The recovered solution (30.0 g) contained the following product selectivities: 13% for C-7 primary amine, 6% for C-7 alcohol, 8% for C-14 primary amine, and 9% for C-14 alcohol. The olefin conversion was 47%.

EXAMPLE 6

The same experimental procedures were repeated and the mixture of $Co_2(CO)_8$ (0.68 g, 2 mmoles), n-$Bu_3P$ (3.2 g, 16 mmoles), 1-hexene (20.0 g), p-dioxane (20 g) and ammonia (20.0 g) were charged. The conditions were 2000 psi, $CO/H_2 = 1:2$ 180° C. and 6 hours. The recovered solution (39.4 g) contained the following product selectivities: 18% for C-7 primary amine, 10% for C-7 alcohol, 11% for C-14 primary amine and 7% for C-14 alcohol. The conversion of olefin was 69%.

EXAMPLE 7

A glass-lined pressure reactor (300 ml) fitted with mechanical stirring was charged with a mixture of dicobalt octacarbonyl (0.68 g, 2.0 mmole) tributylphosphine (3.20 g, 16.0 mmole), 1-hexene (20.0 g) and p-dioxane (20.0 g). The reactor was purged with air, then charged with anhydrous ammonia (20.0 g) and syngas ($CO/H_2$, 1:2) to 100 psi. The reactor was heated to 180° C. while it was agitated by stirring. The pressure was brought up to 2000 psi by the addition of $CO/H_2$ (1:2) mixture. The reaction was held at temperature for 6 hours and the reactor allowed to cool to room temperature. Excess gas was vented from the reactor and 48.5 g of liquid product was recovered.

The product liquid was analyzed by glc. The 1-hexene conversion was calculated to be 56%. The principal products and their selectivities were assigned as follows:

$C_7$ - Primary Amine - 26%
$C_7$ - Primary Alcohol - 8%
$C_{14}$ - Primary Amine - 5%
$C_{14}$ - Primary Alcohol - 7%

What is claimed is:
1. A process for synthesis of $C_{14}$ primary amines comprising reacting 1-hexene, carbon monoxide, hydrogen and anhydrous ammonia in the presence of a catalyst comprising dicobalt octacarbonyl and a triphenylphosphine ligand in p-dioxane solvent at a temperature of 50° C. to 300° C. and a pressure of 500 psig to 2000 psig.
2. The process of claim 1 wherein said primary amine synthesis is conducted in the presence of acetamide.

* * * * *